United States Patent
Jackman

(10) Patent No.: US 6,222,045 B1
(45) Date of Patent: Apr. 24, 2001

(54) PROCESS FOR MANUFACTURING SUBSTITUTED TRIAZOLINONES

(75) Inventor: Dennis E. Jackman, Prairie Village, KS (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/665,092

(22) Filed: Sep. 20, 2000

(51) Int. Cl.[7] .................................................. C07D 249/12
(52) U.S. Cl. ............................................................ 548/263.6
(58) Field of Search .......................................... 548/263.6

(56) References Cited

U.S. PATENT DOCUMENTS

| | | | |
|---|---|---|---|
| 5,594,148 | 1/1997 | Wroblowsky et al. | 548/263.6 |
| 5,599,945 | 2/1997 | Wroblowsky et al. | 548/263.6 |
| 5,606,070 | 2/1997 | Wroblowsky et al. | 548/263.6 |
| 5,708,183 | 1/1998 | Wroblowsky et al. | 548/263.8 |
| 5,917,050 | 6/1999 | Conrad et al. | 548/263.6 |

OTHER PUBLICATIONS

STN International, File CAPLUS, Chemical Abstracts Service, (Columbus, Ohio), 1984, No. 1984:174284; abstract of JP 58–222067.*

* cited by examiner

*Primary Examiner*—Michael G. Ambrose
(74) *Attorney, Agent, or Firm*—Joseph C. Gil

(57) ABSTRACT

The present invention relates to a process for manufacturing substituted triazolinones, which are intermediates in the preparation of herbicidally active compounds. In particular, this invention relates to the reaction of an isothiocyanate with an alkanol to produce a thionocarbamate intermediate product; alkylation of the intermediate product, reaction of the alkylated intermediate with and alkoxycarbobyl or aryloxycarbonyl hydrazine and reaction of the resultant compound with a base to produce a substituted triazolinone. In this context the terms "alkanol" and "alkylation" represent generic terms and thus, include the use of alkanols and alkylating agents having an alkyl group, an alkenyl group, an alkynyl group, a cycloalkyl group, a cycloalkylalkyl group, an aryl group or an arylalkyl group.

15 Claims, No Drawings

PROCESS FOR MANUFACTURING SUBSTITUTED TRIAZOLINONES

TECHNICAL FIELD OF THE INVENTION

The present invention relates to a process for manufacturing substituted triazolinones, which are intermediates in the preparation of herbicidally active compounds. In particular, this invention relates to the reaction of an isothiocyanate with an alkanol to produce a thionocarbamate intermediate product; the alkylation of this thionocarbamate intermediate product to produce an amino intermediate product; the reaction of this amino intermediate product with an alkoxycarbonyl or aryloxycarbonyl hydrazine to produce a substituted triazolinone. In this context, the terms "alkanol" and "alkylation" represent generic terms and thus, include the use of alkanols and alkylating agents having an alkyl group, an alkenyl group, an alkynyl group, a cycloalkyl group, a cycloalkylalkyl group, an aryl group or an arylalkyl group.

In a preferred embodiment, the invention relates to the reaction of a methyl isothiocyanate with methanol, the methylation of the resultant intermediate and the reaction of the intermediate with methyl cabazate to produce a 5-methoxy-4-methyl-2,4-dihydro-3H-1,2,4-triazol-3-one.

BACKGROUND OF THE INVENTION

Triazolinones are well known in the art, as are processes for their preparation and use as herbicides. U.S. Pat. No. 5,708,183 describes a process for the preparation of substituted triazolinones by reacting triazolinethiones with methyl iodide, in the presence of an acid binding agent, and then heating the alkylthiodiazole derivative with hydrogen peroxide in the presence of acetic acid. U.S. Pat. No. 5,917,050 describes a process for the preparation of alkoxytriazolinones by reacting thioimidodicarboxylic diesters with hydrazine, hydrazine hydrate or an acid adduct of hydrazine, in the presence of a diluent and a basic reaction auxiliary.

Further, U.S. Pat. Nos. 5,606,070; 5,599,945; and 5,594,148; each describes a process for the preparation of alkoxytriazolinones which includes reacting iminothiocarbonic diesters with carbazinic esters, and then subjecting the resultant semicarbazide derivatives to a cyclizing condensation reaction.

However, these prior art processes produce triazolinones in unsatisfactory yield and purity. Thus, there is a need in the art for a process to manufacture substituted triazolinones in high yield and purity.

BRIEF SUMMARY OF INVENTION

The present invention is related to a process for the preparation of substituted triazolinones. The process broadly comprises a) reacting an isothiocyanate of the formula (I)

wherein $R^1$ represents an unsubstituted or substituted alkyl, alkenyl, alkynyl, cycloalkyl, cycloalkylalkyl, arylalkyl or aryl,
with an alkanol of the formula (II)

wherein $R^2$ represents an unsubstituted or substituted alkyl, alkenyl, alkynyl, cycloalkyl, cycloalkylalkyl, arylalkyl or aryl, in the presence of a catalytic amount of base, to produce a thionocarbamate intermediate product of the following general formula (III)

wherein $R^1$ and $R^2$ are as defined above, b) reacting the intermediate product of formula (III) with an alkylating agent of the formula (IV)

$$R^3—X \qquad (IV)$$

wherein X represents a halogen, $—O—SO_2—O—R^3$, or $—O—CO—O—R^3$ and
$R^3$ represents an unsubstituted or substituted alkyl, alkenyl, alkynyl, cycloalkyl, cycloalkylalkyl, aryl or arylalkyl, in the presence of a base, to produce an imino intermediate product of the formula (V)

wherein $R^1$, $R^2$ and $R^3$ are as defined above, and c) reacting the intermediate product of formula (V) with a compound of the formula (VI)

$$H_2N—NH—CO_2—R^4 \qquad (VI)$$

wherein $R^4$ represents an alkyl or an aryl, in the presence of a catalytic amount of an acid to produce a product of the formula (VII)

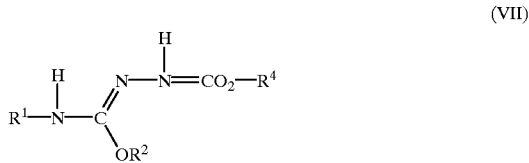

wherein $R^1$, $R^2$ and $R^4$ are each as defined above, and d) reacting the intermediate product of formula (VII) with a catalytic amount of a base to produce a final product of the formula (VIII)

wherein $R^1$ and $R^2$ are each as defined above.

DETAILED DESCRIPTION OF THE INVENTION

The present invention relates to a process for manufacturing substituted triazolinones, which are intermediates in the preparation of herbicidally active compounds. In the context of the invention, the terms "alkanol" and "alkylation" represent generic terms and thus, include the use of alkanols and alkylating agents having an alkyl group, an alkenyl group, an alkynyl group, a cycloalkyl group, a cycloalkylalkyl group, an aryl group or an arylalkyl group.

The process of the present invention includes the step of reacting an isothiocyanate of the formula (I)

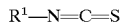    (I)

wherein
   $R^1$ represents an unsubstituted or substituted alkyl, alkenyl, alkynyl, cycloalkyl, cycloalkylalkyl, arylalkyl or aryl,
with an alkanol of the formula (II)

    (II)

wherein
   $R^2$ represents an unsubstituted or substituted alkyl, alkenyl, alkynyl, cycloalkyl, cycloalkylalkyl, arylalkyl or aryl,
in the presence of a catalytic amount of base, to produce a thionocarbamate intermediate product of the formula (III)

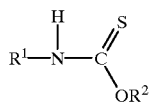    (III)

wherein $R^1$ and $R^2$ are as defined above.

The intermediate product of the general formula (III) is then reacted with an alkylating agent of the following general formula (IV)

    (IV)

wherein
   X represents a halogen, $-O-SO_2-O-R^3$, or $-O-CO-O-R^3$,
   $R^3$ represents an unsubstituted or substituted alkyl, alkenyl, alkynyl, cycloalkyl, cycloalkylalkyl, aryl or arylalkyl,
in the presence of a base, to produce an imino intermediate product of the following general formula (V)

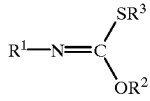    (V)

wherein
   $R^1$, $R^2$ and $R^3$ are as defined above.
The intermediate product of the formula (V) is then reacted with an alkoxycarbonyl or aryloxycarbonyl compound of the formula (VI)

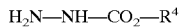    (VI)

wherein $R^4$ represents an alkyl or an aryl, in the presence of a catalytic amount of an acid to produce a product of the formula (VII)

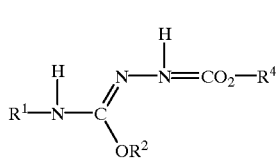    (VII)

wherein $R^1$, $R^2$ and $R^4$ are each as defined above.

The intermediate product of formula (VII) is then reacted with a catalytic amount of a base to produce a final product of the formula (VIII)

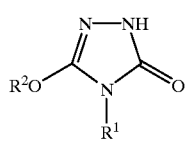    (VIII)

wherein $R^1$ and $R^2$ are each as defined above.

In a preferred embodiment of the invention,
   $R^1$ and $R^2$ each represents an alkyl group, an alkenyl group or an alkynyl group having in each case up to 6 carbon atoms, and each of which is unsubstituted or substituted by cyano, halogen or $C_1$–$C_4$-alkoxy, or
      represents a cycloalkyl group having 3 to 6 carbon atoms or a cycloalkylalkyl group having 3 to 6 carbon atoms in the cycloalkyl moiety and 1 to 4 carbon atoms in the alkyl moiety, each of which is unsubstituted or substituted by halogen or $C_1$–$C_4$-alkyl, or
      represents an aryl group having 6 or 10 carbon atoms or an arylalkyl group having 6 or 10 carbon atoms in the aryl moiety and 1 to 4 carbon atoms in the alkyl moiety, each of which is unsubstituted or substituted by carboxyl, nitro, cyano, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl,
   $R^3$ represents an alkyl, alkenyl or alkynyl, each of which has up to 6 carbon atoms and each of which is unsubstituted or substituted by cyano, halogen or $C_1$–$C_4$-alkoxy, or
      represents a cycloalkyl having 3 to 6 carbon atoms or a cycloalkylalkyl having 3 to 6 carbon atoms in the cycloalkyl moiety and 1 to 4 carbon atoms in the alkyl moiety, each of which is unsubstituted or substituted by halogen or $C_1$–$C_4$-alkyl, or
      represents an aryl having 6 to 10 carbon atoms or an arylalkyl having 6 or 10 carbon atoms in the aryl moiety and 1 to 4 carbon atoms in the alkyl moiety, each of which is unsubstituted or substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl, and
   $R^4$ represents an alkyl having up to 6 carbon atoms, and each of which is unsubstituted or substituted by cyano, halogen or $C_1$–$C_4$-alkoxy, or
      represents an aryl group having 6 or 10 carbon atoms, each of which is unsubstituted or substituted by carboxyl, nitro, cyano, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

More preferably,

R$^1$ and R$^2$ each represents methyl, ethyl, n- or i-propyl, n-, i-, s-, or t-butyl, each of which is unsubstituted or substituted by cyano, fluorine, chlorine or bromine, methoxy or ethoxy, or represents propenyl, butenyl, propinyl or butinyl, each of which is unsubstituted or substituted by cyano, fluorine, chlorine or bromine, or represents cyclopropyl or cyclopropylmethyl, each of which is unsubstituted or substituted by fluorine, chlorine, bromine, methyl or ethyl, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl, R$^3$ represents methyl, ethyl, n- or i-propyl or n-, i-, s- or t-butyl, each of which is unsubstituted or substituted by cyano, fluorine, chlorine or bromine, methoxy or ethoxy, or represents propenyl, butenyl, propinyl or butinyl, each of which is unsubstituted or substituted by cyano, fluorine, chlorine or bromine, or represents cyclopropyl, cyclobutyl or cyclopropylmethyl, each of which is unsubstituted or substituted by fluorine, chlorine, bromine, methyl or ethyl, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl, and R$^4$ represents methyl, ethyl, n- or i-propyl or n-, i-, s- or t-butyl, each of which is unsubstituted or substituted by cyano, fluorine, chlorine or bromine, methoxy or ethoxy, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

Most preferably,

R$^1$, R$^2$, R$^3$ and R$^4$ each represents methyl.

The process of the invention may be conducted as a one pot process, without isolation of the intermediate product of formula (III).

The process according to the invention is generally carried out at atmospheric pressure. However, it is also possible to conduct the process under elevated or reduced pressure.

The reaction of the isothiocyanate with the alkanol is carried out at a temperature of from about −20° C. to about 20° C., and preferably at a temperature of from about 0° C. to about 5° C. In this context, the term "alkanol" (formula II) is used as a generic term and thus, expressly includes the above definition of R$^2$. This reaction is carried out in the presence of a catalytic amount of base.

Suitable bases include customary inorganic bases, organic bases and acid acceptors. These include alkali metal and alkaline earth metal acetates, amides, carbonates, bicarbonates, hydrides, hydroxides, alkoxides and alcoholates such as, for example, sodium acetate, potassium acetate, calcium acetate and ammonium acetate, lithium amide, sodium amide, potassium amide and calcium amide, sodium carbonate, potassium carbonate and calcium carbonate, sodium bicarbonate, potassium bicarbonate and calcium bicarbonate, lithium hydride, sodium hydride, potassium hydride and calcium hydride, lithium hydroxide, sodium hydroxide, potassium hydroxide and calcium hydroxide, sodium methoxide, potassium methoxide, sodium ethoxide, potassium ethoxide, sodium n- and i-propoxide and potassium n- and i-propoxide, sodium n-, i-, s- and t-butoxide and potassium n-, i-, s- and t-butoxide, sodium methylate, sodium ethylate, and potassium tert-butylate, and also basic organic nitrogen compounds such as trimethylamine, triethylamine, tripropylamine, tributylamine, ethyl diisopropylamine, N,N-dimethyl-cyclohexylamine, dicyclohexylamine, ethyl-dicyclohexylamine, N,N-dimethyl-aniline, N,N-dimethyl-benzyl-amine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabi-cyclo[2.2.2]-octane (DABCO), 1,5-diazabicyclo[4.3.0]-non-5-ene (DBN), and 1,8-diazabicyclo[5.4.0]-undec-7-ene (DBU).

Preferred bases for use in the process of the invention are sodium hydroxide and potassium hydroxide.

In one embodiment of the invention, the reaction of the isothiocyanate and the alkanol may be carried out in the presence of a solvent. Suitable solvents include aliphatic, alicyclic and aromatic, unhalogenated and halogenated hydrocarbons such as, for example, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran and ethylene glycol dimethyl ether and ethylene glycol diethyl ether; ketones such as acetone, butanone, and methyl isobutyl ketone; nitriles such as acetonitrile, propionitrile and butyronitrile; amides such as N,N-dimethylformamide, N,N-dimethylacetamide, N-methyl-formanilide, N-methyl-pyrrolidone and hexamethylphosphoric triamide; esters such as methyl acetate and ethyl acetate; sulfoxides such as dimethyl sulfoxide; alcohols such as methanol, ethanol, n- or i-propanol, n-, i-, s- and t-butanol, ethylene glycol monomethyl ether, ethylene glycol monoethyl ether, diethylene glycol monomethyl ether, diethylene glycol monoethyl ether; water; and mixtures thereof.

Preferred solvents include methyl isobutyl ketone, water, methanol, propanol, and a commercially available mixture of xylenes containing ethylbenzene, ortho-xylene, para-xylene and meta-xylene.

In the process of the invention, the resulting thionocarbamate intermediate product (formula III) is then reacted with the alkylating agent (formula IV). The alkylation of the intermediate compound of the formula (III) proceeds with high selectivity on the S atom. In this context, the terms "alkylation" and "alkylating agent" (formula IV) are used as generic terms and thus, expressly include the above definition of R$^3$.

The alkylation reaction is carried out at a temperature of from about −10° C. to about 20° C., and preferably at a temperature of from about −5° C. to about 5° C. This reaction is carried out in the presence of a base. The base for use in the alkylation step of the present invention includes customary inorganic bases, organic bases and acid acceptors. These include alkali metal and alkaline earth metal acetates, amides, carbonates, bicarbonates, hydrides, hydroxides, alkoxides and alcoholates such as, for example, sodium acetate, potassium acetate, calcium acetate and ammonium acetate, lithium amide, sodium amide, potassium amide and calcium amide, sodium carbonate, potassium carbonate and calcium carbonate, sodium bicarbonate, potassium bicarbonate and calcium bicarbonate, lithium hydride, sodium hydride, potassium hydride and calcium hydride, lithium hydroxide, sodium hydroxide, potassium hydroxide and calcium hydroxide, sodium methoxide, potassium methoxide, sodium ethoxide, potassium ethoxide, sodium n- and i-propoxide and potassium n- and i-propoxide, sodium n-, i-, s- and t-butoxide and potassium n-, i-, s- and t-butoxide, sodium methylate, sodium ethylate, and potassium tert-butylate, and also basic organic nitrogen compounds such as trimethylamine, triethylamine, tripropylamine, tributylamine, ethyl diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN) and 1,8-diazabicyclo[5.4.0]-undec-7-ene (DBU).

Suitable alkylating agents for use in the process of the present invention include compounds of the general formula (IV) as defined above. Preferred alkylating agents include methyl bromide, dimethyl sulfate and methyl chloride.

In one embodiment of the invention, the alkylation reaction is carried out in the presence of a solvent. Suitable solvents for use in the alkylation reaction of the present invention include aliphatic, alicyclic and aromatic, unhalogenated and halogenated hydrocarbons such as, for example, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran and ethylene glycol dimethyl ether and ethylene glycol diethyl ether; ketones such as acetone, butanone, and methyl isobutyl ketone; nitriles such as acetonitrile, propionitrile or benzonitrile; amides such as N,N-dimethylformamide, N,N-dimethyl-acetamide, N-methylformanilide, N-methyl-pyrrolidone and hexamethyl-phosphoric triamide; esters such as methyl acetate and ethyl acetate, sulphoxides such as dimethyl sulphoxide, alcohols such as methanol, ethanol, n- and i-propanol, n-, i-, s-, and t-butanol, ethylene glycol monomethyl ether, ethylene glycol monoethyl ether, diethylene glycol monomethyl ether, diethylene glycol monoethyl ether; water and mixtures thereof.

Preferred solvents include methyl isobutyl ketone, water, methanol, propanol and a commercially available mixture of xylenes containing ethylbenzene, ortho-xylene, para-xylene, meta-xylene.

The reaction of the resulting imino intermediate product (formula V) with the compound of the formula (VI) is carried out at a temperature of from about −5° C. to about 20° C., and preferably from about 0° C. to about 5° C. This reaction is carried out in the presence of a catalytic amount of acid. Suitable acids for use in the present invention include mineral acids and organic acids. Preferred acids include hydrochloric, sulfuric and phosphoric acids.

The resulting compound of the formula (VII) is then reacted with a catalytic amount of base to produce a substituted triazolinone of the formula (VIII). This reaction is carried out at a temperature of from about 5° C. to about 70° C., and preferably from about 40° C. to about 50° C. Suitable bases include customary inorganic bases, organic bases and acid acceptors. These include alkali metal and alkaline earth metal acetates, amides, carbonates, bicarbonates, hydrides, hydroxides, alkoxides and alcoholates such as, for example, sodium acetate, potassium acetate, calcium acetate and ammonium acetate, lithium amide, sodium amide, potassium amide and calcium amide, sodium carbonate, potassium carbonate and calcium carbonate, sodium bicarbonate, potassium bicarbonate and calcium bicarbonate, lithium hydride, sodium hydride, potassium hydride and calcium hydride, lithium hydroxide, sodium hydroxide, potassium hydroxide and calcium hydroxide, sodium methoxide, potassium methoxide, sodium ethoxide, potassium ethoxide, sodium n- and i-propoxide and potassium n- and i-propoxide, sodium n-, i-, s- and t-butoxide and potassium n-, i-, s- and t-butoxide, sodium methylate, sodium ethylate, and potassium tert-butylate, and also basic organic nitrogen compounds such as trimethylamine, triethylamine, tripropylamine, tributylamine, ethyl diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN) and 1,8-diazabicyclo[5.4.0]-undec-7-ene (DBU).

In another embodiment, a nitrogen flow is maintained through the reaction mixture.

Further, in a preferred embodiment, 5-methoxy-4-methyl-2,4-dihydro-3H-1,2,4-triazol-3-one (MMT) is produced by reacting methyl isothiocyanate with methanol, alkylating with methyl bromide and reacting with methyl carbazate.

The invention is further illustrated but is not intended to be limited by the following examples in which all parts and percentages are by weight unless otherwise specified.

EXAMPLES

Example 1

In a 500 ml round bottom flask equipped with a stirrer, thermometer, condenser and addition funnel, a mixture of 40 grams (0.547 mole) of methylisothiocyanate in 180 ml of methanol was added over a time period of 20 minutes to 100 ml of methanol containing about 6 grams of 50% sodium hydroxide. An ice bath was used to maintain a temperature of from about 0° C. to about 5° C. During the next 20 minutes, an additional 38.5 grams of 50% sodium hydroxide (0.556 moles total) was added dropwise to the reaction mixture followed by the addition of 30 ml of water. The mixture was then treated with about 60 grams (0.63 mole) of methyl bromide at a temperature of from about −5° C. to about 5° C. The mixture was stirred for about 30 minutes at a temperature of from about 0° C. to about 5° C. The ice bath was removed and the mixture was allowed to warm to room temperature. After about 2 hours, the mixture was cooled to a temperature of from about 0° C. to about 5° C., and then the pH was adjusted to about 7.3 with concentrated hydrochloric acid, and about 47 grams (0.522 mole) of methylcarbazate was added followed by another 9 grams of concentrated hydrochloric acid. The mixture was stirred at ice bath temperature overnight, then 50.5 grams (0.506 mole) of 50% sodium hydroxide was added slowly at a temperature of from about 5° C. to about 10° C.

The mixture was heated for about 2 hours at 50° C., then the methanol was stripped off under vacuum at 65° C. The mixture was cooled to a temperature of from about 0° C. to 5° C. and the mixture was acidified to a pH of about 6.6 with concentrated hydrochloric acid, which gave a white crystalline mass which was filtered, washed with ice water, and air dried to give 49.8 grams (about 71%) of the product.

Example 2

The process of Example 1 was repeated with the exception that 2.4 grams of sodium was used as a catalyst for the first step instead of the 6 grams of 50% sodium hydroxide. In addition, the initial mixture of methylisothiocyanate, sodium, and methanol was allowed to stand overnight before the sodium hydroxide was added to the mixture. The resultant yield was 55.4 grams (about 78.5%) of the product.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a substituted triazolinone comprising steps of:

a) reacting an isothiocyanate of the formula (I)

  (I)

wherein
$R^1$ represents an unsubstituted or substituted alkyl, alkenyl, alkynyl, cycloalkyl, cycloalkylalkyl, aryl or arylalkyl, with an alkanol of the formula (II)

  (II)

wherein
$R^2$ represents an unsubstituted or substituted alkyl, alkenyl, alkynyl, cycloalkyl, cycloalkylalkyl, aryl or arylalkyl, in the presence of a catalytic amount of base, to produce a thionocarbamate intermediate product of the formula (III)

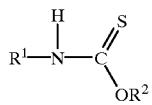  (III)

wherein
$R^1$ and $R^2$ are as defined above; and b) reacting the intermediate product of formula (III) with an alkylating agent of the formula (IV)

  (IV)

wherein
X represents a halogen, $—O—SO_2—O—R^3$, or $—O—CO—O—R^3$,
$R^3$ represents an unsubstituted or substituted alkyl, alkenyl, alkynyl, cycloalkyl, cycloalkylalkyl, aryl or arylalkyl,
in the presence of a base, to produce an imino intermediate product of the formula (V)

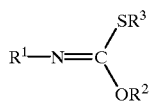  (V)

wherein
$R^1$, $R^2$ and $R^3$ are as defined above, and c) reacting the intermediate product of formula (V) with a compound of the formula (VI)

  (VI)

wherein
$R^4$ represents an alkyl or an aryl, in the presence of a catalytic amount of an acid to produce a compound of the formula (VII)

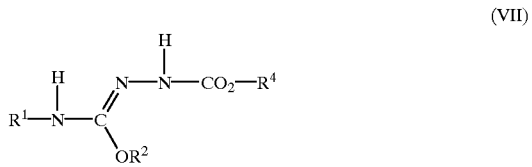  (VII)

wherein
$R^1$, $R^2$ and $R^4$ are each as defined above; and d) reacting the product of the formula (VII) with a catalytic amount of a base to produce a substituted triazolinone of the formula (VIII)

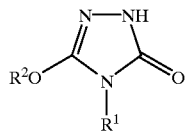  (VIII)

wherein
$R^1$ and $R^2$ are each as defined above.

2. The process of claim 1 wherein the reaction in step a) is carried out at a temperature of from about $-20°$ C. to about $20°$ C.

3. The process of claim 1 wherein the reaction in step b) is carried out at a temperature of from about $-10°$ C. to about $20°$ C.

4. The process of claim 1 wherein the reaction in step c) is carried out at a temperature of from about $-5°$ C. to about $20°$ C.

5. The process of claim 1 wherein the reaction in step d) is carried out at a temperature of from about $5°$ C. to about $70°$ C.

6. The process of claim 1 wherein the reaction in steps a) and b) are carried out in the presence of a solvent.

7. The process of claim 6 wherein the solvent is selected from the group consisting of aliphatic, alicyclic and aromatic, unhalogenated and halogenated hydrocarbons, ethers, ketones, nitriles, esters, sulfoxides, amides, alcohols, water and mixtures thereof.

8. The process of claim 1 wherein a nitrogen flow is maintained through the reaction mixture.

9. The process of claim 1 wherein the base recited in steps a), b) and d) is selected from the group consisting of alkali metal acetates, alkaline earth metal acetates, amides, carbonates, bicarbonates, hydrides, hydroxides, alkoxides and alcoholates.

10. The process of claim 9 wherein the base is sodium hydroxide.

11. The process of claim 1 wherein the alkylating agent is selected from the group consisting of dimethyl sulfate, methyl chloride and methyl bromide.

12. The process of claim 1 wherein steps a), b), c) and d) are carried out via a one-pot process without separation of the intermediate products.

13. The process of claim 1 wherein the triazolinone product of formula (VIII) is 5-methoxy-4-methyl-2,4-dihydro-3H-1,2,4-triazol-3-one (MMT).

14. The process of claim 1 wherein the acid in step c) is selected from the group consisting of a mineral acid and an organic acid.

15. The process of claim 1 wherein the acid in step c) is selected from the group consisting of hydrochloric acid, sulfuric acid and phosphoric acid.

* * * * *